(12) United States Patent
Falco et al.

(10) Patent No.: US 8,656,927 B2
(45) Date of Patent: Feb. 25, 2014

(54) EARPLUG

(75) Inventors: Robert Nicolo Falco, Indianapolis, IN (US); Jeffrey L. Hamer, Springville, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/618,580

(22) Filed: Sep. 14, 2012

(65) Prior Publication Data
US 2013/0019880 A1 Jan. 24, 2013

Related U.S. Application Data

(63) Continuation of application No. 12/781,159, filed on May 17, 2010, now Pat. No. 8,291,911, and a continuation of application No. 29/337,641, filed on May 27, 2009, now abandoned.

(51) Int. Cl.
*A61F 11/00* (2006.01)
(52) U.S. Cl.
USPC ........................................ 128/864
(58) Field of Classification Search
USPC ........... 128/864, 866; 181/129–130, 134–135
See application file for complete search history.

(56) References Cited

U.S. PATENT DOCUMENTS

| | | |
|---|---|---|
| D124,880 S | 1/1941 | Teunisz |
| 3,005,564 A | 10/1961 | Weichselbaum |
| 3,020,333 A | 2/1962 | Bangert et al. |
| 3,850,361 A | 11/1974 | Day et al. |
| D237,853 S | 12/1975 | Katz |
| D247,160 S | 2/1978 | LaCroce et al. |
| D248,873 S | 8/1978 | Raitto |
| D254,446 S | 3/1980 | Raitto |
| D265,129 S | 6/1982 | Leight |
| D267,429 S | 12/1982 | Harada |
| D267,512 S | 1/1983 | Carlsson et al. |
| 4,375,016 A | 2/1983 | Harada |
| 4,541,377 A | 9/1985 | Amos |
| 4,576,430 A | 3/1986 | Dufresne |
| D321,128 S | 10/1991 | DeBose, Jr. |
| 5,074,375 A | 12/1991 | Grozil |
| 5,080,110 A | 1/1992 | Weldon |
| D372,070 S | 7/1996 | Zak et al. |
| 5,564,431 A | 10/1996 | Seward |

(Continued)

FOREIGN PATENT DOCUMENTS

| | | |
|---|---|---|
| CA | 18732 | 8/1952 |
| EP | 568217 | 9/2006 |
| WO | 2004/021941 | 3/2004 |

*Primary Examiner* — Tatyana Zalukaeva
*Assistant Examiner* — Camtu Nguyen
(74) *Attorney, Agent, or Firm* — Craig A. Deutsch

(57) ABSTRACT

An earplug is provided and includes a tip for use in forward and lateral sealing, which is formed to define a rearward recessed cavity, and a stem. The stem includes a user graspable elongate portion configured with a stiffness in a first direction that is greater than a stiffness in a second direction, which is transverse to the first direction, and a member, disposed at a forward end of the elongate portion and configured to be insertable into the cavity, the member including a surface to be adhered to an interior facing surface of the cavity and on which a channel is defined to allow for outflow from the cavity, and the member being formed with a shape to complement that of the cavity to axially and circumferentially align the tip and the stem.

5 Claims, 9 Drawing Sheets

(56) References Cited

U.S. PATENT DOCUMENTS

| | | |
|---|---|---|
| D377,493 S | 1/1997 | Oda |
| 5,607,152 A | 3/1997 | Strassburger |
| D398,531 S | 9/1998 | De Vries |
| D399,212 S | 10/1998 | Roderwiess |
| D412,118 S | 7/1999 | Rodea |
| D432,604 S | 10/2000 | Scheiner |
| D435,330 S | 12/2000 | Soergel |
| 6,226,865 B1 | 5/2001 | Tanikawa et al. |
| 6,234,812 B1 | 5/2001 | Ivers et al. |
| D443,259 S | 6/2001 | Okubo |
| D444,141 S | 6/2001 | Koss et al. |
| 6,252,164 B1 | 6/2001 | Wise |
| D445,694 S | 7/2001 | Gans |
| D445,774 S | 7/2001 | Matsuoka |
| D451,401 S | 12/2001 | Silvers et al. |
| 6,439,413 B1 | 8/2002 | Prevot et al. |
| D462,185 S | 9/2002 | Sandy |
| D463,392 S | 9/2002 | Khadivar |
| 6,457,969 B1 | 10/2002 | Khosla |
| D466,995 S | 12/2002 | Knauer et al. |
| D467,363 S | 12/2002 | West |
| 6,568,394 B2 * | 5/2003 | Falco .................. 128/864 |
| D479,832 S | 9/2003 | Homewood et al. |
| D486,815 S | 2/2004 | Jones |
| D489,007 S | 4/2004 | Hall et al. |
| D497,191 S | 10/2004 | Shore |
| D500,021 S | 12/2004 | Hu |
| D512,409 S | 12/2005 | Ishizaki |
| D518,728 S | 4/2006 | Frantz |
| D519,870 S | 5/2006 | Pritchard |
| D521,637 S | 5/2006 | Yang |
| D523,345 S | 6/2006 | Kamineni |
| D524,655 S | 7/2006 | Baez |
| D526,564 S | 8/2006 | Slavin et al. |
| D526,981 S | 8/2006 | Kim et al. |
| D528,213 S | 9/2006 | Darley et al. |
| D529,822 S | 10/2006 | Munn |
| D531,056 S | 10/2006 | Ioannides et al. |
| D531,517 S | 11/2006 | Hillard |
| D531,586 S | 11/2006 | Poulet |
| D532,400 S | 11/2006 | DeZhang |
| D536,262 S | 2/2007 | Ioannides et al. |
| D536,264 S | 2/2007 | Ioannides et al. |
| D538,361 S | 3/2007 | Sato |
| D538,600 S | 3/2007 | Jennewein et al. |
| D542,153 S | 5/2007 | Farrow et al. |
| D542,656 S | 5/2007 | Szczesniak |
| D546,706 S | 7/2007 | Ioannides et al. |
| D549,596 S | 8/2007 | Ioannides et al. |
| D554,603 S | 11/2007 | Murakami |
| D559,382 S | 1/2008 | Sanpei |
| D561,715 S | 2/2008 | Sugiyama |
| D561,732 S | 2/2008 | Motoishi |
| D562,987 S | 2/2008 | Colin et al. |
| D564,824 S | 3/2008 | Henry |
| D568,743 S | 5/2008 | Kunesh et al. |
| D569,253 S | 5/2008 | Cracchiolo |
| D572,206 S | 7/2008 | Ikeda et al. |
| D575,427 S | 8/2008 | Nelson et al. |
| D578,394 S | 10/2008 | Shurtleff et al. |
| D581,286 S | 11/2008 | White |
| D581,289 S | 11/2008 | Westphal |
| D582,285 S | 12/2008 | Cracchiolo |
| D584,152 S | 1/2009 | VerWeyst et al. |
| D585,402 S | 1/2009 | Shimizu |
| D585,558 S | 1/2009 | Feeley et al. |
| D586,666 S | 2/2009 | Lucido |
| D587,378 S | 2/2009 | Powers et al. |
| D588,936 S | 3/2009 | Ioannides et al. |
| D590,055 S | 4/2009 | Butler et al. |
| D592,300 S | 5/2009 | Yeh |
| D593,858 S | 6/2009 | Kubicek et al. |
| D594,117 S | 6/2009 | Patzer et al. |
| D595,268 S | 6/2009 | Kolton |
| D595,837 S | 7/2009 | Benner |
| D596,500 S | 7/2009 | Diss et al. |
| D596,956 S | 7/2009 | Diss et al. |
| D596,957 S | 7/2009 | Diss |
| D599,829 S | 9/2009 | Jorgensen |
| D599,907 S | 9/2009 | Mulvey et al. |
| D603,715 S | 11/2009 | Diaz |
| D604,611 S | 11/2009 | Ames et al. |
| D605,172 S | 12/2009 | Seade |
| D606,050 S | 12/2009 | Nousiainen |
| D608,767 S | 1/2010 | Liner |
| D611,344 S | 3/2010 | Longacre |
| D611,821 S | 3/2010 | Gabrielsson et al. |
| D611,835 S | 3/2010 | Huang |
| D611,929 S | 3/2010 | Blanchard |
| D612,249 S | 3/2010 | Wurster et al. |
| D613,862 S | 4/2010 | Vue et al. |
| D614,049 S | 4/2010 | Diss et al. |
| D614,955 S | 5/2010 | Diss |
| D616,747 S | 6/2010 | Stull et al. |
| D616,979 S | 6/2010 | Falco |
| D617,191 S | 6/2010 | Stull et al. |
| D620,366 S | 7/2010 | Bruscha et al. |
| D620,377 S | 7/2010 | Diss |
| D621,030 S | 8/2010 | Falco |
| D621,271 S | 8/2010 | Soni |
| D622,591 S | 8/2010 | Biesecker et al. |
| D622,837 S | 8/2010 | Falco |
| D623,286 S | 9/2010 | Falco |
| D627,019 S | 11/2010 | Martin |
| D633,196 S | 2/2011 | Falco |
| D641,465 S | 7/2011 | Falco |
| 8,291,911 B2 | 10/2012 | Falco |
| 2004/0129276 A1 | 7/2004 | Kuno et al. |
| 2006/0067551 A1 * | 3/2006 | Cartwright et al. ........... 381/322 |

* cited by examiner

EARPLUG

CROSS REFERENCE TO RELATED APPLICATIONS

This application is a continuation of U.S. Ser. No. 29/337,641 filed May 27, 2009, now abandoned, which is a continuation of U.S. Ser. No. 12/781,159, now issued as U.S. Pat. No. 8,291,911, the disclosures of which are incorporated by reference in their entirety herein.

BACKGROUND OF THE INVENTION

The subject matter disclosed herein relates to earplugs and a method of assembling an earplug.

Hearing protection devices (HPDs) may be broadly categorized into earplugs, which are placed into or against an entrance of an ear canal of a user to form a seal and block sound (insert or semi-insert), earmuffs, which fit over and around the ear (circumaural) to provide an acoustic seal against the head, and helmets, which normally encase the entire head of the user. Earplugs are typically made from materials such as slow-recovery closed-cell foam, vinyl, silicone, elastomer formulations, spun fiberglass and cotton/wax combinations. They may be grouped into the categories of foam earplugs, pre-molded earplugs, formable earplugs, custom molded earplugs and semi-insert earplugs.

Foam earplugs are generally made from either slow-recovery PVC or polyurethane closed-cell material, both of which provide similar amounts of sound attenuation. PVC earplugs are commonly punched from sheets of foam to have simple contours with parallel sides and cylindrical or hexagonal footprints. Polyurethane earplugs are molded to have shapes like bullets or bells and may have asymmetrical features like ridges. Since their introduction, foam earplugs have become widely used because they are generally comfortable to wear and they provide a high degree of amount of sound attenuation. They can, however, be difficult for some users to insert fully and properly.

Pre-molded earplugs, on the other hand, are formed from flexible materials, including foam, into conical, bulbous or other shapes and are typically affixed to or enshroud a flexible stem for handling and insertion. Users can, therefore, grip the stem and push the earplugs into place in the ear canal whereupon an acoustic (pneumatic) seal is made against the canal walls.

Foam earplugs or pre-molded earplugs can, therefore, be used by students taking tests who want to have an amount of ambient sound attenuated or by musicians in concert, flight deck personnel or employees on the floor of a manufacturing plant who are exposed to extremely loud sounds that would otherwise impair their hearing after prolonged exposures. In each case, the effectiveness of the earplugs depends greatly on the amount and types of sounds that are attenuated, the comfort users experience when the earplugs are worn, the ability of the users to insert their earplugs safely into their ear canals and the ability of the users to remove their earplugs safely when desired.

Often, however, the factors that relate to the effectiveness of earplugs can be in conflict with one another. For example, an earplug whose tip is very dense may attenuate a large amount of sound but may also be very uncomfortable to wear. Meanwhile, an earplug that is less dense may be very forgiving but may not attenuate a sufficiently large amount of sound and could be difficult to insert properly. Similarly, an earplug that comes equipped with a relatively stiff stem may be easy to insert into an ear canal, but the same earplug may be dangerous if the stem were subject to an impact that forced the earplug deep into the ear canal.

BRIEF DESCRIPTION OF THE INVENTION

According to one aspect of the invention, an earplug is provided and includes a tip for use in forward and lateral sealing, which is formed to define a rearward recessed cavity, and a stem, including a user graspable elongate portion configured with a stiffness in a first direction that is greater than a stiffness in a second direction, which is transverse to the first direction, and a member, disposed at a forward end of the elongate portion and configured to be insertable into the cavity, wherein the member includes a surface to be adhered to an interior facing surface of the cavity and on which a channel is defined to allow for outflow from the cavity, and the member is formed with a shape to complement that of the cavity to axially and circumferentially align the tip and the stem.

According to another aspect of the invention, an earplug is provided and includes a tip for use in forward and lateral sealing, which is formed to define a rearward recessed cavity, and a stem, including a user graspable elongate portion configured with a stiffness in a first direction that is greater than a stiffness in a second direction, which is transverse to the first direction, and a member, disposed at a forward end of the elongate portion, which is configured to be insertable into the cavity with axial and circumferential alignment and to be adhered to an interior facing surface thereof.

According to yet another aspect of the invention, an earplug is provided and includes a tip for use in forward and lateral sealing, which is formed to define a rearward recessed cavity, and a stem, including a user graspable elongate portion, and a member, disposed at a forward end of the elongate portion and configured to be insertable into the cavity, wherein the member includes a surface to be adhered to an interior facing surface of the cavity and on which a channel is defined to allow for outflow from the cavity, and the member is formed with a shape to complement that of the cavity to axially and circumferentially align the tip and the stem.

According to yet another aspect of the invention, a method of assembling an earplug is provided and includes forming a tip for use in forward and lateral sealing, boring a rearward recessed cavity into the tip from a rear face thereof, forming a stem with a biaxial stiffness including an elongate portion, and a member, disposed at a forward end of the elongate portion and configured to be insertable into the cavity, defining a channel along a surface of the member, aligning the member with the cavity, and adhering the surface of the member to an interior facing surface of the cavity with outflow from the cavity being urged along the channel.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
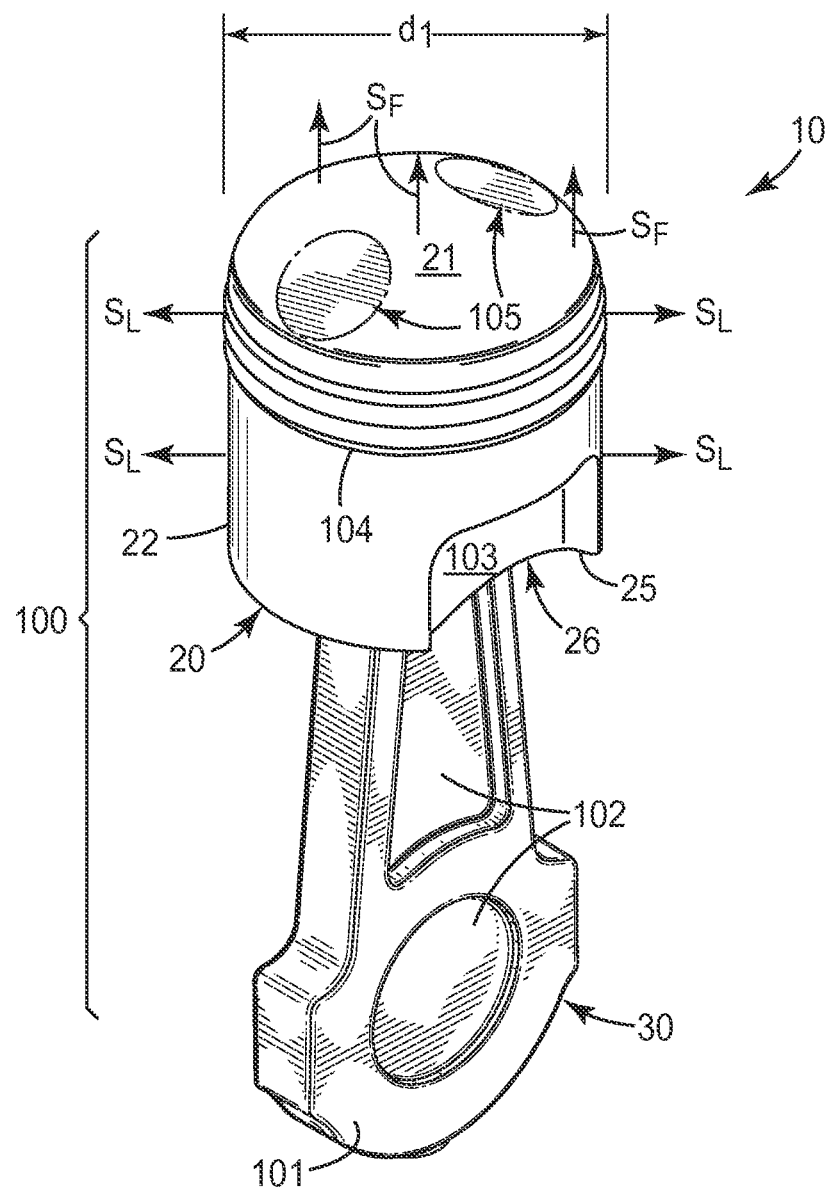
FIG. 1 is a perspective view of an earplug in accordance with embodiments of the invention.

With reference to FIG. 1, an earplug 10 is provided. The earplug 10 includes a tip 20 and a stem 30. The tip 20 can be inserted into the ear canal of a user whereupon sound attenuating material of the tip 20 forms an acoustic or pneumatic seal against the walls of the ear canal. The seal serves to attenuate a given amount of sound in accordance with a type and a density of the sound attenuating material in use and the ability of the user to properly insert the earplug 10. The earplug 10 can, therefore, protect the user's inner ear components from, for example, loud sounds associated with the floor of a manufacturing plant. The stem 30 is user manipulated and allows the user to grasp the earplug 10 when pushing the tip 20 into and through the ear canal.

The sound attenuating material of the tip 20 may be polymer foam or the like and has a normal non-deformed diameter, $d_1$, which is generally wider than a width of an ear canal for a human being. For the small minority of people (2-10% of the general population) whose ear canals are either relatively narrow or relatively wide, $d_1$ can be decreased or increased. Thus, the tip 20 can be provided so as to fit snugly in the ear canal of most people with the polymer foam acting as an acoustic or pneumatic sealant against undesirable noise levels.

In accordance with embodiments of the invention, the polymer foam has a density range between about 5 to about 20 lb/ft³ with an optimum density range of about 9 to about 15 lb/ft³. Thus, the polymer foam is easily deformable by the user and tends to rebound following the deformation. In this way, the tip 20 may be inserted with appropriate force into the ear canal whereupon the polymer foam adaptively responds to the shape and the size of the ear canal interior and freely articulates with respect to the stem 30.

The adaptive response of the tip 20 to the shape and size of the ear canal interior can be manifested as inward and outward deformations of the polymer foam that arise from pressure applied to the tip 20 by the ear canal walls. The free articulation of the polymer foam can be manifested as radial deformations of the polymer foam that arise from torsion forces applied by the user in opposition to frictional forces present between the ear canal walls and the exterior surface of the tip 20.

The tip 20 is formed with a forward portion 21 of sound attenuating material and lateral portions 22 of sound attenuating material. As such, the forward portion 21 of the tip 20 provides sealing to the ear canal of the user in the forward, $S_F$, sealing direction as the tip 20 is inserted into the ear canal. Similarly, the lateral portions 22 of the tip 20 provide sealing to the ear canal in the lateral, $S_L$, sealing directions. With reference to FIGS. 1, 5, 7 and 11, the tip 20 is further formed with a rear face 25. A rearward facing recessed cavity 26 bores into the tip 20 from the rear face 25 in the forward direction.

Figure 13:
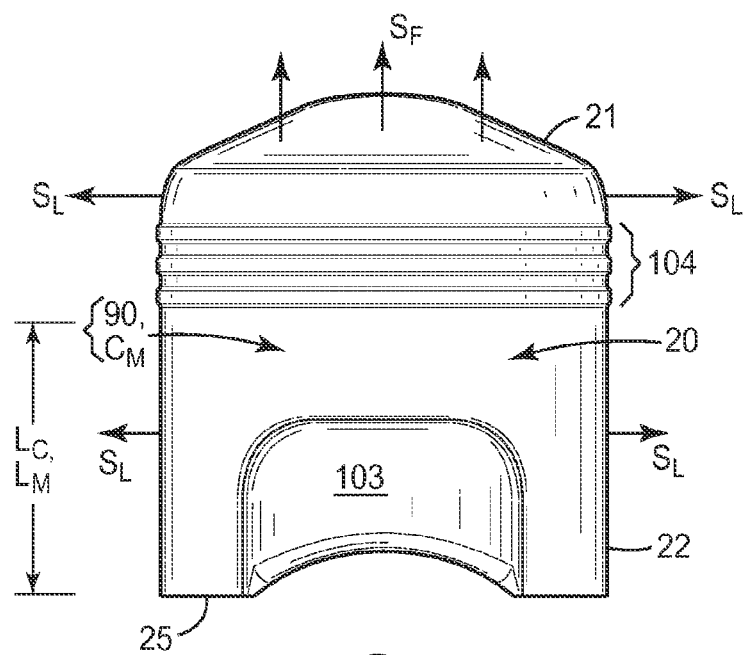
FIG. 13 is a side sectional view of an earplug tip in accordance with embodiments of the invention.
Figure 14:
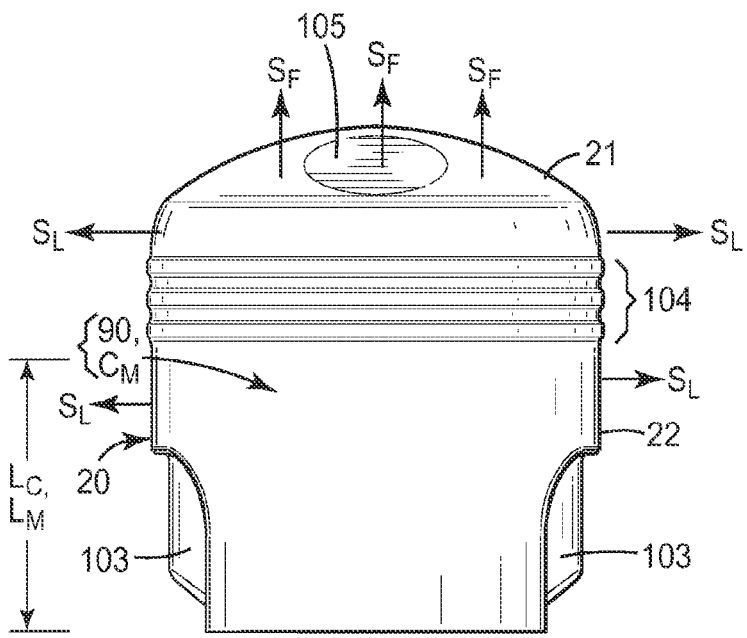
FIG. 14 is an alternate side sectional view of an earplug tip in accordance with embodiments of the invention.

As shown in FIGS. 13 and 14, the tip 20 also includes a center of mass, $C_M$, that resides within the tip 20 at axial position 90. In accordance with an embodiment of the invention, the cavity 26 is recessed from the rear face 25 by a length, $L_c$, toward the forward portion 21 and extends through to an interior portion of the tip 20 that is disposed between the $C_M$ at axial position 90 and the forward portion 21.

Figure 6:
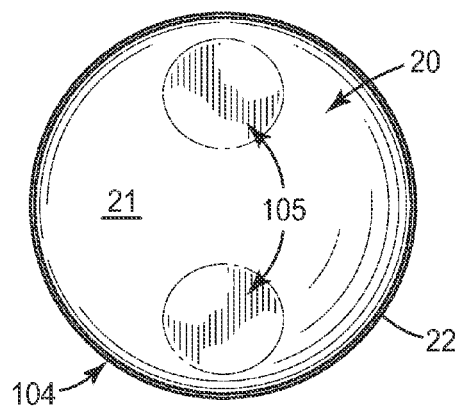
FIG. 6 is a rear facing axial view of an earplug tip in accordance with alternate embodiments of the invention.
Figure 7:
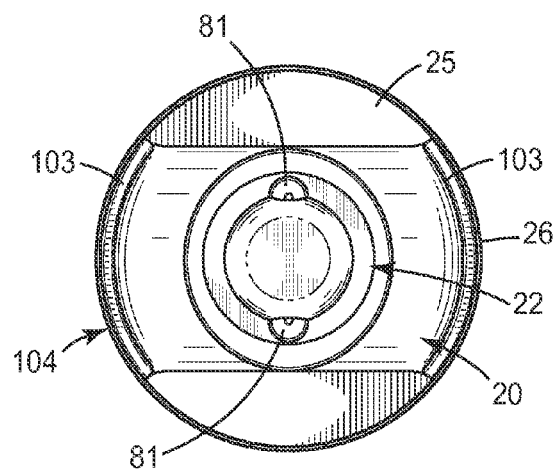
FIG. 7 is a forward facing axial view of an earplug tip cavity in accordance with alternate embodiments of the invention.

As will be discussed below, the tip 20 may be formed with variable shapes and/or designs. For example, the tip 20 may resemble a piston with the forward portion 21 resembling a piston dome. Further, the tip 20 can include additional design elements, such as wrist pin bores 103, ring lands and grooves 104 and piston dome features 105 (see FIG. 6).

Figure 2:
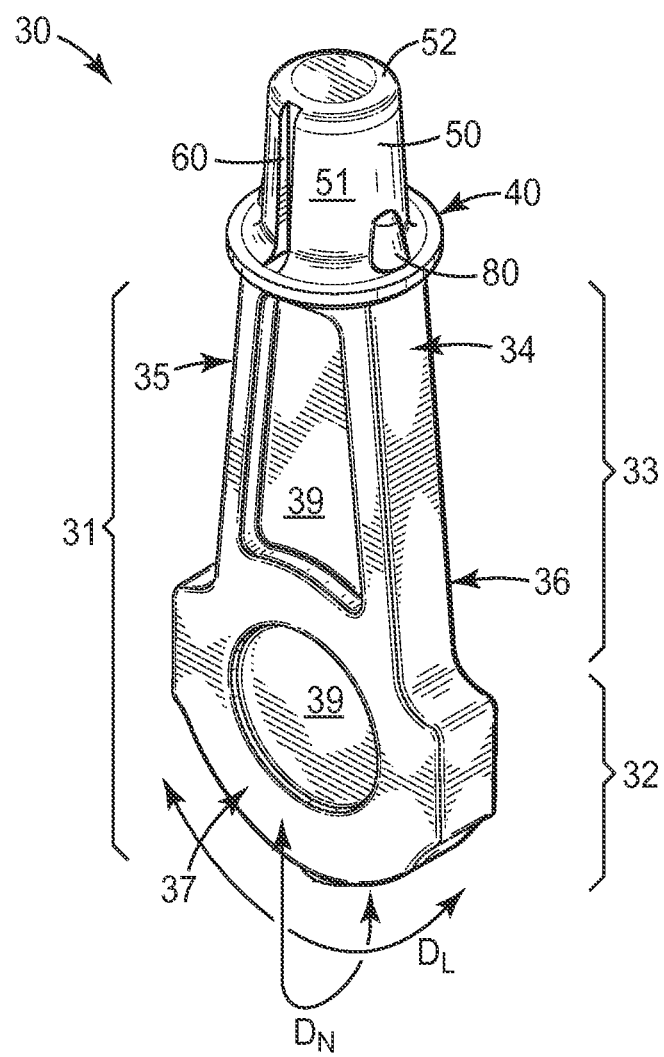
FIG. 2 is a perspective view of an earplug stem in accordance with embodiments of the invention.
Figure 3:
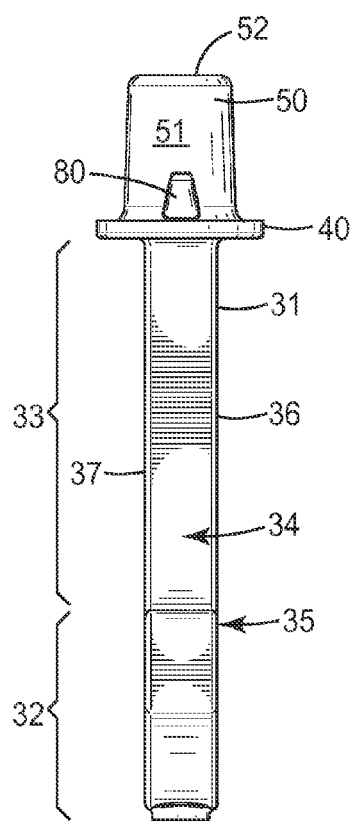
FIG. 3 is a side sectional view of the earplug stem of FIG. 2 in accordance with embodiments of the invention.
Figure 4:
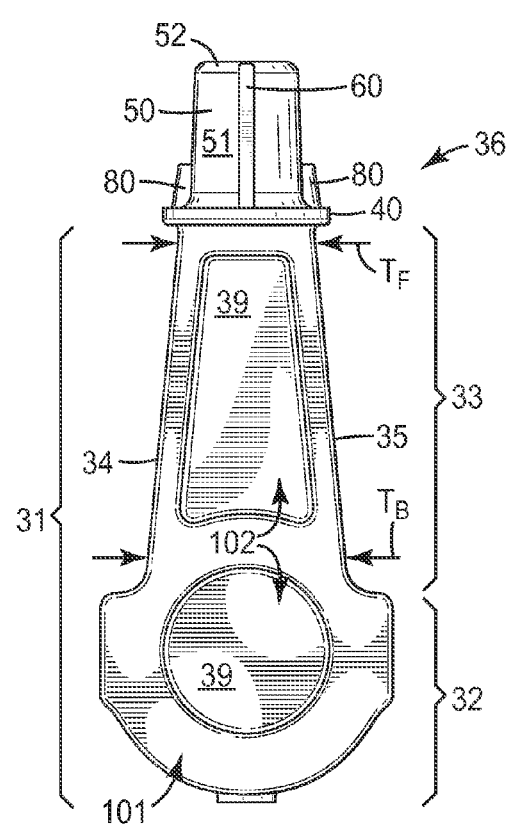
FIG. 4 is an elevational view of the earplug stem of FIG. 2 in accordance with embodiments of the invention.
Figure 5:
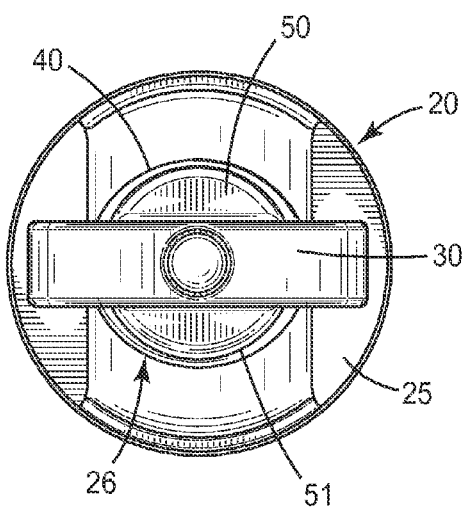
FIG. 5 is a forward facing axial view of the earplug stem of FIG. 2 and an earplug tip in accordance with embodiments of the invention.

With reference to FIGS. 2, 3 and 4 and in an embodiment of the invention, the stem 30 includes an elongate portion 31, a member 50 and a flange 40 delimiting a boundary between the elongate portion 31 and the member 50. The elongate portion 31 includes a base section 32 and a tapered section 33. As shown in FIG. 2, the base section 32 may be generally bulbous, however, it is to be understood that this shape is merely exemplary and that the base section 32 may be provided in multiple shapes. The tapered section 33 extends integrally from the base section 32 to the flange 40 and is tapered along the longitudinal axis from sidewall 34 to sidewall 35 while faces 36 and 37 remain generally parallel with one another. Undercut portions 39, positioned on the faces 36 and 37 of both the base section 32 and the tapered section 33, allow the stem 30 to be relatively easily gripped by the user.

With reference to FIG. 4 and, in an exemplary embodiment, the tapered section 33 can have a first thickness, $T_B$, which is disposed proximate to the base section 32 and a second thickness, $T_F$, which is disposed proximate to the flange 40. As shown in FIG. 4, the first thickness, $T_B$, is generally thicker than the second thickness, $T_F$. As such, with the tip 20 being formed to resemble a piston, the tapered section 33 of the stem 30 may similarly resemble a rod of a rod and piston combination. In this way, the faces 36 and 37 and the undercut portions 39 of both the base section 32 and the tapered section 33 can be formed as rod faces 101 and rod structural features 102.

Referring back to FIG. 2, with the above-described configuration, the elongate portion 31 provides a biaxial stiffness that promotes a safe insertion of the tip 20 into the ear canal. The biaxial stiffness is characterized in that the stiffness of the elongate portion 31 in the lateral direction, $D_L$, is greater than the stiffness of the elongate portion 31 in the normal direction, $D_N$, which is transverse to the lateral direction, $D_L$. The relative stiffness of the elongate portion 31 in the lateral direction, $D_L$, allows a user to encourage the forward procession of the tip 20 into and through the irregular shape of the user's ear canal. Conversely, the relative lack of stiffness in the normal direction, $D_N$, allows the elongate portion 31 to bend when the tip 20 encounters ear canal resistance and the ear canal walls impinge upon the tip 20. Thus, as the user pushes the earplug 10 into and through the ear canal, the earplug 10 is able to move relatively efficiently through the ear canal walls and it is unlikely that the user will push the tip 20 unsafely deep into the ear canal. Similarly, should the stem 30 be subject to an impact force with the earplug 10 fully inserted into the ear canal, it is likely that the stem 30 will bend in the normal direction, $D_N$, such that injury to the inner ear of the user is prevented.

The member 50 is the component of the stem 30 that is inserted into the cavity 26 when the earplug 10 is assembled. The member 50 generally extends integrally from the flange 40 along a longitudinal direction in parallel with that of the stem 30. The member 50 includes a surface 51 that is to be adhered to the sound attenuating material of the tip 20 that is located at the interior facing surface of the cavity 26 when the member 50 is inserted therein. An adhesive, such as Loctite 403 glue, can be used to cause the surface 51 to adhere to the interior facing surface of the cavity 26.

A channel 60 is defined as a crevice in the surface 51 and may run along the longitudinal length of the member 50. The channel 60 allows for an outflow of air and excess adhesive from the cavity 26 when the member 50 is inserted therein. The channel 60 may be provided as a single channel or, more commonly, as a pair of channels disposed on opposite sides of the member 50. Of course, it is to be understood that still further additional channels 60 can be provided on the surface 60. Moreover, the cavity 26 can also include channels of its own.

While the channel 60 is illustrated as being straight, it is to be understood that the channel 60 may have various shapes and sizes that are either regular or irregular. For example, the channel 60 could be straight, as shown in FIGS. 2 and 4, or curved or threaded around the member 50.

Figure 8:
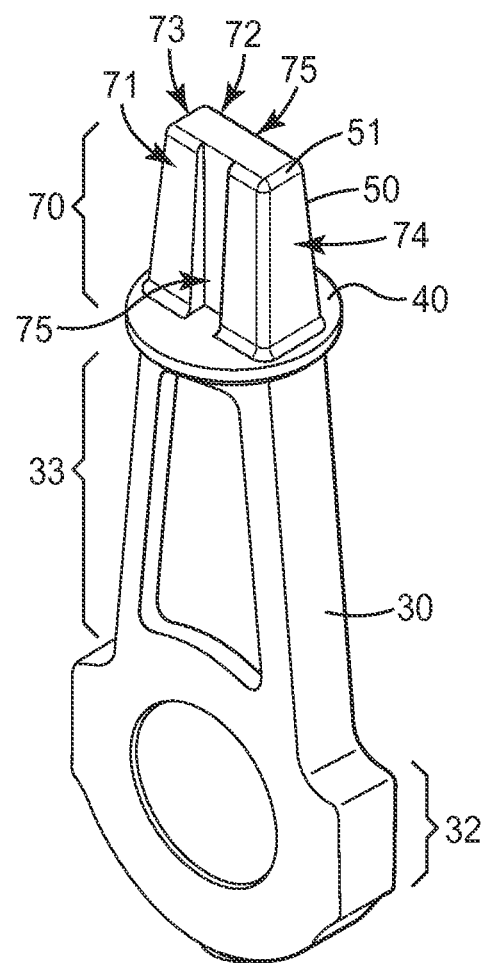
FIG. 8 is a perspective view of an earplug stem in accordance with alternate embodiments of the invention.
Figure 9:
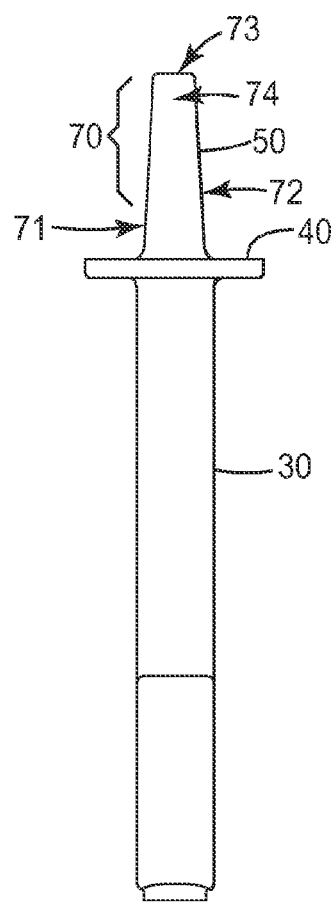
FIG. 9 is a side sectional view of the earplug stem of FIG. 8 in accordance with embodiments of the invention.
Figure 10:
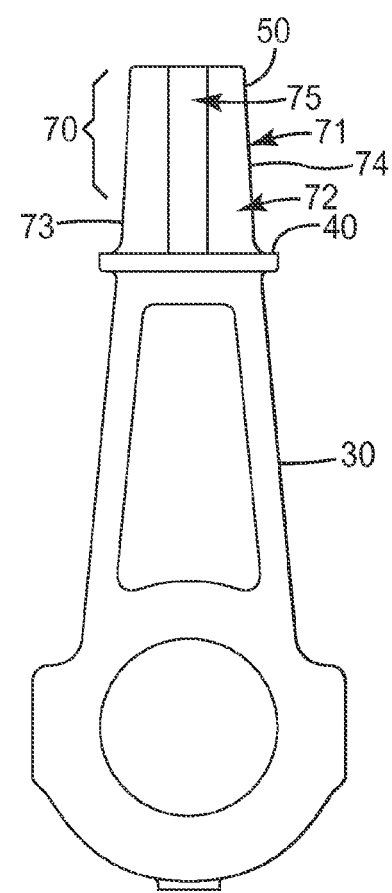
FIG. 10 is an elevational view of the earplug stem of FIG. 8 in accordance with embodiments of the invention.
Figure 11:
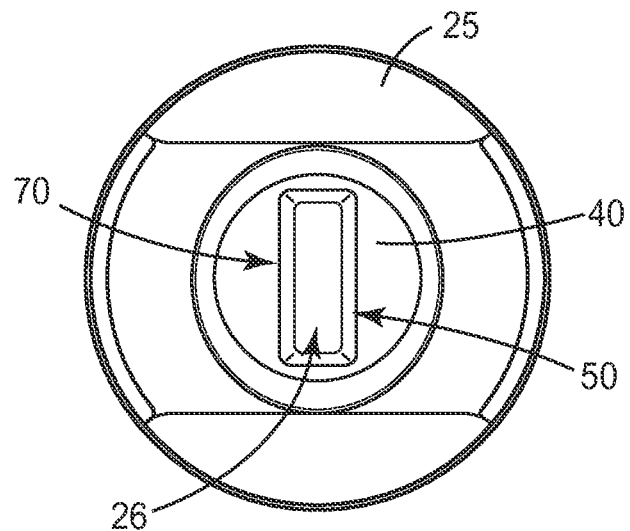
FIG. 11 is a forward facing axial view of an earplug tip in accordance with embodiments of the invention.
Figure 12:
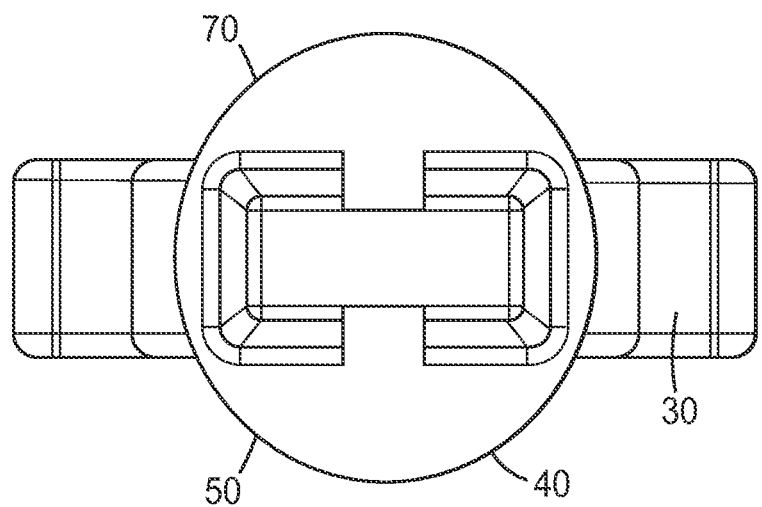
FIG. 12 is an axial view of the earplug stem of FIG. 8.

With reference to FIGS. 2 and 8, the member 50 is formed with a shape that complements the shape of the cavity 26 and, in some embodiments, a length, $L_M$, that complements the length, $L_C$, of the cavity 26. In this way, the tip 20 and the stem 30 can be axially and circumferentially aligned with one another when the member 50 is inserted into the cavity 26. As examples, as shown in FIG. 2, the member 50 may be formed with a rounded shape, and, as shown in FIG. 8, the member 50 may be formed with a rectangular shape 70. In both cases, the cavity 26 is formed with complementary rounded and rectangular shapes as well.

In detail, as shown in FIGS. 2-7, the member 50 and the cavity 26 may each be rounded with the member 50 further including tabs 80 and the cavity 26 being further defined with pockets 81 into which the tabs 80 are receivable when the member 50 is inserted into the cavity 26. In both cases, the member 50 and the cavity 26 can be additionally tapered in the forward direction to at least aid in the ease of the insertion of the member 50 into the cavity 26.

Conversely, as shown in FIGS. 8-12, the member 50 and the cavity 26 may each be formed with rectangular shapes. In these cases, the member 50 includes opposing faces 71 and 72 and sidewalls 73 and 74 that extend between the faces 71 and 72. Channels 75 are defined along the longitudinal length of the member 50, although they may have various shapes and sizes as discussed above, and positioned generally within a central portion of each of the faces 71 and 72. Again, the member 50 and the cavity 26, being rectangular, can be additionally tapered in the forward direction to at least aid in the ease of the insertion of the member 50 into the cavity 26.

With the member 50 and the cavity 26 having complementary shapes that axially and circumferentially align the tip 20 and the stem 30, the earplug 10 is further provided with increased structural stability. That is, with the respective shapes of the member 50 and the cavity 26 complementing one another, a potential for relative rotation between the stem 30 and the tip 20 when the user rotates the stem 30 during, e.g., the insertion of the tip 20 into the ear canal, is reduced. In this way, while the exterior of the tip 20 may freely articulate with respect to the stem 30, once the earplug is removed from the ear canal or reoriented therein, the tip 20 will be urged to rebound to its original form.

In addition, the complementary shapes of the member 50 and the cavity 26 provide stability to the earplug 10 while the adhesive bonding the surface 51 of the member 50 to the cavity 26 sets. This allows the member 50 and the cavity 26 to be aligned with one another for appearance purposes. With the tip 20 and the stem 30 so aligned, the achievement of an accurate rod and piston design, for example, is promoted.

In accordance with an embodiment of the invention, as mentioned above, the member 50 and the cavity 26 are extendable through the tip 20 and beyond at least a center of mass, CM, 90 of the tip 20 such that an end of the cavity 26 and the distal end 52 of the member 50 are disposed between the CM 90 and the forward portion 21 when the member 50 is inserted into the cavity 26. This configuration tends to prevent undesirable deformation of the tip 20, such as a folding of the tip 20 over itself.

This configuration also increases an ability of the sound attenuating material of the tip 20 to acoustically seal the ear canal. When the tip 20 is inserted in the ear canal, the member 50 acts as a relatively rigid central body that impinges against the sound attenuating material of the tip 20 in opposition to the forces applied by the ear canal walls upon the sound attenuating material in an inward direction. The opposing forces counterbalance one another and increase the acoustic sealing provided by the tip 20. Thus, with the distal end 52 of the member 50 disposed between the CM 90 and the forward portion 21, a relatively large amount of the forces applied by the ear canal walls are counterbalanced by the extension of the member 50 into the tip 20. At the same time, the presence of the forward portion 21 of the tip 20 increases user comfort by protecting the inner components from abutment with the relatively rigid structure of the member 50.

As mentioned above, the flange 40 serves to delimit a boundary between the elongate portion 31 and the member 50 and extends in an outward radial direction from the forward end of the elongate portion 31 and a rear end of the member 50. The flange 40 is generally positioned such that the member 50 is sufficiently long to fully inhabit the cavity 26 when the member 50 is installed therein. Also, the flange 40 serves as an additional surface for adhesion to the tip 20 or, alternately, to deflect the outflow of excess adhesive flowing along the channel 60 from the cavity 26.

In accordance with an embodiment of the invention, the tip 20 and the stem 30 may be formed to resemble any desired image. In particular, where the earplug is intended for use in an automobile manufacturing plant, the tip 20 and the stem 30 can appropriately resemble a rod and piston combination. Here, as mentioned above, the tip 20 may include design elements, such as wrist pin bores 103, ring lands and grooves 104 and piston dome features 105, while the stem 30 may include design elements, such as rod faces 101 and rod structural features 102. Of course, such designs are merely exemplary and other shape and size options are available.

Figure 15:
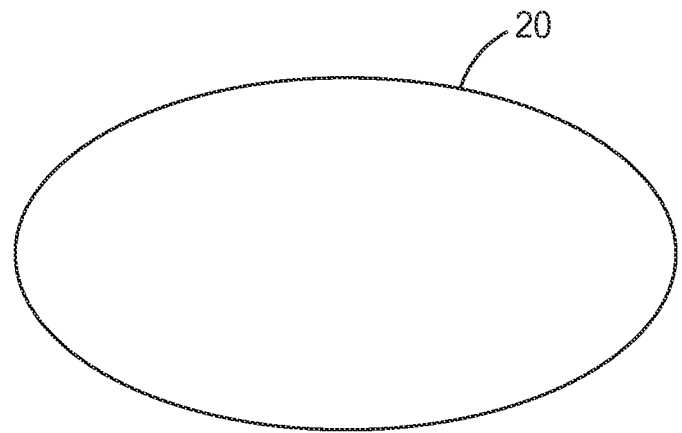
FIG. 15 is a sectional view of an exemplary tip having an oval cross-section.

In accordance with further embodiments of the invention, the biaxial stiffness of the stem 30 is directed such that the lateral direction, $D_L$, and the normal direction, $D_N$, are circumferentially aligned with at least one of the circumferential position of the channel 60 around the member 50, the arrangement of the complementary shapes of the member 50 and the cavity 26 and/or the exterior appearance of the tip 20 and the stem 30. That is, where the stem 30 is less relatively stiff in the normal direction, $D_N$, the surface 51 of the member 50 may have channels 60 defined thereon in alignment with faces 36 and 37 and off-phase with respect to sidewalls 34 and 35. In this way, outflow of air and/or excess adhesive can be promoted by a simple bend of the stem 30 in the normal direction, $D_N$. Similarly, where the complementary shapes of the member 50 and the cavity 26 are aligned with the normal direction, $D_N$, the likelihood that the tip 20 and the stem 30 be misaligned during assembly may be reduced. Finally, the exterior appearance of the tip 20 may be irregular or, for example, the tip 20 may have oval cross-section that corresponds to the shape of an ear canal, viewed in FIG. 15, for example. In such a case, having the normal direction, $D_N$, be aligned with the long axis of the tip 20, may encourage the user to take advantage of the oval shape of the tip 20 while inserting the earplug 10 into his/her ear canal by bending the stem 30 only about the faces 36 and 37 and the long sides of the tip 20.

In accordance with yet another aspect of the invention, a method of assembling an earplug is provided and includes forming a polymer foam tip 20, for use in forward and lateral sealing with a rearward recessed cavity 26, forming a stem 30 with a biaxial stiffness including an elongate portion 31, and a member 50, and inserting the member 50 into the cavity 26. The member 50 is disposed at a forward end of the elongate portion 31 and is configured to be insertable into the cavity 26. The member 50 includes a surface 51 to adhere to an interior facing surface of the cavity 26. A channel 60 is defined on the surface 51 to allow for outflow from the cavity 26 when the member 50 is inserted therein. The member 50 is formed with a shape to complement that of the cavity 26 to axially and circumferentially align the tip 20 and the stem 30 when the member 50 is inserted into the cavity 26. The inserting of the member 50 into the cavity 26 is achieved such that adhesive adheres the surface 51 to the interior facing surface of the cavity 26 and such that outflow proceeds from the cavity 26 along the channel 60.

In an alternate embodiment, the stem 30 is held with the member 50 placed in a given position. The polymer foam of the tip 20 is then formed around the member 50 such that the polymer foam adheres to the surface 51 of the member 50. Here, the flow channel 60 allows air exhausted from the formation of the polymer foam, to flow out from the cavity 26.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. An earplug, comprising:
a sound attenuating tip having an oval cross-section and defining a rearward recessed cavity including a pocket; and
a stem, comprising:
a user graspable elongate portion configured with a stiffness in a first direction that is greater than a stiffness in a second direction, which is transverse to the first direction, and
a member, disposed at a forward end of the elongate portion, positioned in the cavity, the member including a protrusion;
wherein the protrusion of the member is positioned in the pocket of the recessed cavity such that the first direction and the second direction are circumferentially aligned.

2. The earplug according to claim 1, wherein the elongate portion comprises opposing sidewalls tapered toward one another and opposing faces extending between the sidewalls, which are arranged substantially in parallel.

3. The earplug according to claim 1, wherein the sidewalls taper toward one another in a forward direction.

4. The earplug according to claim 1, wherein the opposing faces are defined with undercut portions recessed therefrom.

5. The earplug according to claim 1, wherein the elongate portion comprises a bulbous user graspable base section at a rear thereof.

* * * * *